United States Patent [19]

Taylor

[11] Patent Number: Plant 6,806

[45] Date of Patent: May 16, 1989

[54] NECTARINE

[75] Inventor: James W. Taylor, Dinuba, Calif.

[73] Assignee: Ito Packing Co., Inc., Reedley, Calif.

[21] Appl. No.: 137,376

[22] Filed: Dec. 22, 1987

[51] Int. Cl.[4] ..... A01H 5/03

[52] U.S. Cl. ..... Plt./40

[58] Field of Search ..... Plt./40

*Primary Examiner*—Robert E. Bagwill

*Attorney, Agent, or Firm*—Dennis B. Haase

[57] ABSTRACT

A new and distinct variety of nectarine tree characterized by a white fleshed, free stone fruit, which is both attractive in appearance and demonstrating good resistance to bruising and a reduced tendency toward browning around bruised areas, and, further, having the characteristic of maturing in the mid-season.

1 Drawing Sheet

BACKGROUND OF THE VARIETY

The present invention relates to a new and distinct variety of nectarine tree, which I refer to as Summer Snow, displaying a white fleshed, freestone fruit, which is both attractive in appearance and having the characteristics of maturing in the mid-season period. This variety was developed from a continued fruit breeding program.

ORIGIN AND ASEXUAL REPRODUCTION OF THE NEW VARIETY

This novel nectarine variety was derived from an ongoing fruit breeding program, having as its purpose, the improvement of nectarines so as to enhance and market acceptability by the consumer. The variety was propagated by taking the flowers of the Red Jim variety (U.S. Plant Pat. No. 4,518) which were emasculated and pollenated with pollen from an unnamed variety supposedly derived from an F2 selection of the cross of Quetta Nectarine×flowering peach. Seeds produced from this procedure were stratified and grown to a height of about 18 inches. These seedlings were then bud grafted into dehorned orchard trees in the experimental orchard of Ito Packing Co., Inc., Reedley, Calif., for testing and selection. Each clone was budded into several limbs to make sure that it propagated true to type.

SUMMARY OF THE NEW VARIETY

The novel variety, which was developed through the above method, was selected because of its excellent eating quality and attractive appearance. The bright red color over the cream base produces fruit which is very attractive to the consumer. Moreover, the fruit, when bruised, has a much less tendency to darken than other white fleshed commercial nectarine varieties, thereby minimizing loss due to handling. The browning, or darkening, of the flesh when slightly bruised has always been a major deterrent in marketing at the retail level, and this variety ameliorates that problem.

The fruit matures about three weeks after Burchel Rose (U.S. Plant Pat. No. 1,421), which it most closely resembles, but is differentiated from this variety by being of larger size, having a much brighter red color and being more resistant to browning as a result of bruising.

BRIEF DESCRIPTION OF THE DRAWING

The accompanying drawing illustrates typical specimens of the fruit and foliage of my new variety as grown in the San Joaquin Valley of California. Two unsectioned specimens are shown, one of which is in side elevation, while the other is a bottom plan view illustrating the suture. Another specimen has been sectioned so that one-half illustrates the color of the flesh and the exposed stone, while the other half shows the fruit with the stone removed.

DETAILED DESCRIPTION

The following is a detailed description of my new variety with color reference being to the Maerz and Paul Dictionary of Colors, except in instances where terminology having generally accepted meaning is employed.

Parentage: Red Jim×Supposed F2 selection of (Quetta×flowering peach).

Propagation: Maintains its distinguishing characteristics through several bud grafts.

Locality where grown and observed: Near Reedley, County of Fresno, Calif.

TREE

Size: Large, spreading, open, vase form.

Vigor: Vigorous, productive.

Regularity of bearing: A regular bearer.

Trunk: Medium size; medium texture.

Branches: Spreading.

Leaves:

- *Color.*—Top side — 31C11; underside 31H10.
- *Size —Average length* 5¼ inches; average width 1¼ inches; medium thickness.
- *Shape.*—Essentially round but may be slightly compressed on ventral suture near apex.
- *Marginal form.*—Glandular; crenate;
- *Glandular characteristics.*—Average number, four; opposite; medium size; reniform; position — usually two on petiole and two to four on leaf blade.
- *Petiole.*—Medium length; medium thickness.
- *Stipules.*—Wanting except when leaves are very young.

Flower bud: Large, showy, pink.

Flower: Large, showy but petals slightly smaller than those of some large flowered nectarines.

*Color.*—Light pink (41E1).

*Date of full bloom.*—With variety Red Jim (U.S. Plant Pat. No. 4,518).

FRUIT

Maturity: When described, eating ripe, about 10 days after Summer Grant (U.S. Plant Pat. No. 2,879).

Date of first picking: July 14, 1987.

Date of last picking: July 20, 1987.

Size: Medium size, average in axial diameter, 2¾ inches. Average suture plane, 2½ inches.

*Uniformity.*—Uniform, symmetrical, globose.

*Axial diameter.*—2¾ inches.

Form: Uniform, symmetrical, globose.

*Tendency to split.*—Seldom has a tendency to split.

*Tendency to crack.*—No tendency to crack.

*Base.*—Round.

*Apex.*—Slightly depressed with pistil point slightly lower than cheeks.

*Suture.*—Extends from the base to beyond the apex. Shallow on the ventral surface but deepens slightly approaching and beyond the apex.

Ventral surface: Equal.

Cavity: Average ¼ inch deep. Almost round but elongated slightly toward the ventral side of the fruit.

Stem: Medium; adheres well to the stone.

Skin:

*Thickness.*—Medium thickness, medium toughness; no tendency to growth crack.

*Down.*—Wanting.

*Color.*—Light cream base color around the cavity and in areas of the fruit densely shaded by foliage (11F1) shading 1112. Fine red speckles cover small portions of the fruit (1110) condensing to red stippled area (5F6) giving way to a dark red (6L5) over color. When fully ripe the over color deepens to a very dark red (55L2).

*Suture stripe.*—None.

Flesh:

*Texture.*—Firm at hard ripe maturity but softening with a very juicy consistency at eating maturity.

*Color.*—White (18A1) with red around the pit cavity and spreading through the flesh around the pit.

*Juice.*—Abundant, rich.

*Flavor.*—Very sweet with little acid.

*Aroma.*—Very pronounced as in many white fleshed varieties.

*Fibers.*—Few.

*Ripening.*—Evenly.

*Eating quality.*—Excellent.

*Amygdalin.*—Moderate.

Stone:

*Adherence to flesh.*—Free stone.

*Size.*—Average thickness ⅝ inch; average width 15/16 inch; average length 1-1/16 inch.

*Form.*—Oval.

*Hilum.*—Small, oblong.

*Dorsal edge.*—Shallow groove, broken up toward apex.

*Ventral edge.*—Shallow grooved.

*Surface.*—Somewhat regularly furrowed toward apex. Irregularly pitted toward base.

*Color.*—Brown (7L12) with red, especially around dorsal area.

*Tendency to split.*—No splitting observed.

Use: Market; dessert.

Keeping quality: Fair.

Shipping quality: Fair.

Resistance to disease: Although the new variety of nectarine tree typically possesses the described characteristics, as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated my new variety of nectarine tree, what is claimed as new and desired to be secured by Letters Patent is:

1. A new and distinct variety of nectarine tree with fruit of white free stone type, substantially as herein shown and described, wherein the novelty is attributable to the bright red color over the cream base, creating an extremely attractive fruit with excellent eating quality and the highly aromatic characteristic of some white fleshed nectarines, further wherein the nearly round shape with the slightly depressed apex help to prevent bruising, the fruit demonstrating a reduced tendency to turn brown around slightly bruised areas providing great advantage in commercial handling of the fruit.

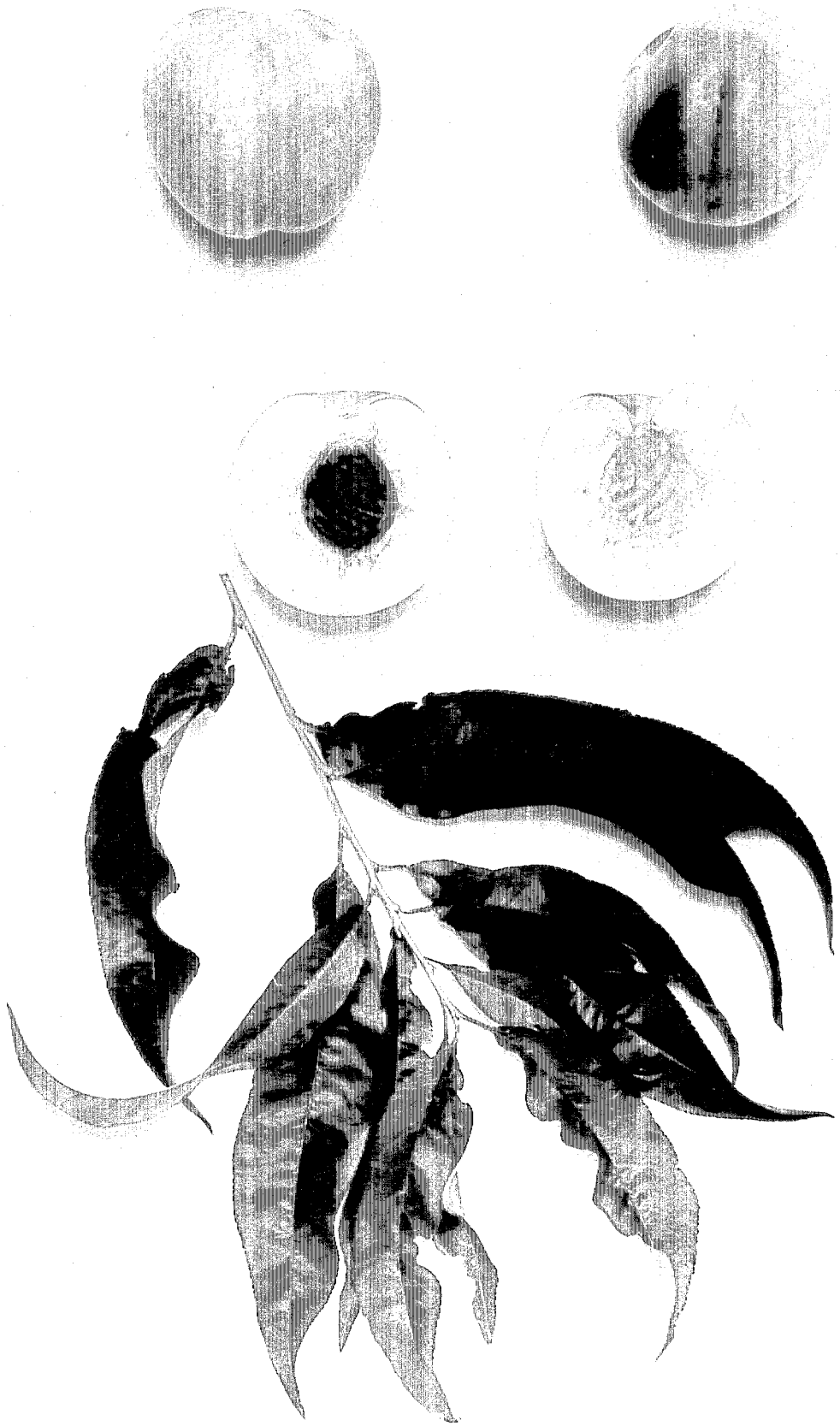

* * * * *